(12) United States Patent
Kang et al.

(10) Patent No.: US 12,075,914 B2
(45) Date of Patent: Sep. 3, 2024

(54) HUMAN BODY DETECTION MAT

(71) Applicant: LG Electronics Inc., Seoul (KR)

(72) Inventors: Hyunoh Kang, Seoul (KR); Hyungyu Park, Seoul (KR); Jeongwook An, Seoul (KR)

(73) Assignee: LG Electronics Inc., Seoul (KR)

( * ) Notice: Subject to any disclaimer, the term of this patent is extended or adjusted under 35 U.S.C. 154(b) by 1060 days.

(21) Appl. No.: 16/926,172

(22) Filed: Jul. 10, 2020

(65) Prior Publication Data

US 2020/0337471 A1     Oct. 29, 2020

Related U.S. Application Data

(63) Continuation of application No. PCT/KR2018/003344, filed on Mar. 22, 2018.

(30) Foreign Application Priority Data

Jan. 10, 2018   (KR) ................. 10-2018-0003506

(51) Int. Cl.
*A47C 21/04*     (2006.01)
*A61B 5/00*      (2006.01)
*A61M 21/02*     (2006.01)

(52) U.S. Cl.
CPC .......... *A47C 21/048* (2013.01); *A61B 5/4815* (2013.01); *A61M 21/02* (2013.01); *A47C 21/04* (2013.01); *A61B 5/4806* (2013.01)

(58) Field of Classification Search
CPC ..... A47C 21/048; A47C 21/04; A61B 5/4815; A61B 5/4806; A61M 21/02

USPC ............................................. 5/421; 219/217
See application file for complete search history.

(56) References Cited

U.S. PATENT DOCUMENTS

| | | | |
|---|---|---|---|
| 11,896,131 B2 * | 2/2024 | Lee ...................... | A47C 21/044 |
| 2007/0008156 A1 | 1/2007 | Ueda et al. | |
| 2020/0337471 A1 * | 10/2020 | Kang .................. | A61B 5/4815 |
| 2021/0307530 A1 * | 10/2021 | Lee ...................... | A47C 21/044 |

FOREIGN PATENT DOCUMENTS

| | | | | |
|---|---|---|---|---|
| DE | 112018006330 T5 * | 8/2020 | ........... | A47C 21/048 |
| KR | 1020120031847 | 4/2012 | | |
| KR | 1020150057184 | 5/2015 | | |
| KR | 1020170028173 | 3/2017 | | |
| KR | 1020170115121 | 10/2017 | | |
| WO | WO-2019139201 A1 * | 7/2019 | ........... | A47C 21/048 |

* cited by examiner

*Primary Examiner* — Robert G Santos
(74) *Attorney, Agent, or Firm* — Fish & Richardson P.C.

(57) ABSTRACT

A human body detection mat is provided to analyze a user's sleep and selectively generate heat in a partial area thereof. The human body detection mat can include a substrate, a plurality of first detection electrode lines arranged on the substrate and formed along a first direction, and a plurality of second detection electrode lines arranged on the substrate and formed along a second direction which intersects with the first direction. The first and second detection electrode lines intersect with each other within a specific area on the substrate and are formed to be flexed within the specific area.

14 Claims, 10 Drawing Sheets

RELATED ART
FIG. 1

RELATED ART

HUMAN BODY DETECTION MAT

CROSS-REFERENCE TO RELATED APPLICATIONS

This application is a continuation of International Application No. PCT/KR2018/003344, filed on Mar. 22, 2018, which claims the benefit of earlier filing date and right of priority to Korean Application No. 10-2018-0003506, filed on Jan. 10, 2018, the contents of which are incorporated herein by reference in their entirety.

TECHNICAL FIELD

The present disclosure relates to a human body detection mat capable of analyzing a user's sleep and selectively heating a partial region of the mat.

BACKGROUND

Sleep is important for physical and mental health. Proper sleep can help reducing fatigue, improving immunity and concentration, relieving stress, reducing inflammation, repairing muscles, and the like.

Accordingly, sleep assistance devices, sleep guidance devices, or sleep analysis devices for assisting in proper and effective sleep have been developed. However, such devices use various sensors that need to be worn on a user's body. This may cause inconvenience to the user in getting proper sleep, and the use of the sensors may be cumbersome. Accordingly, there is an increasing demand for a device capable of analyzing the user's sleep without wearing it on his or her body.

Figure 1:
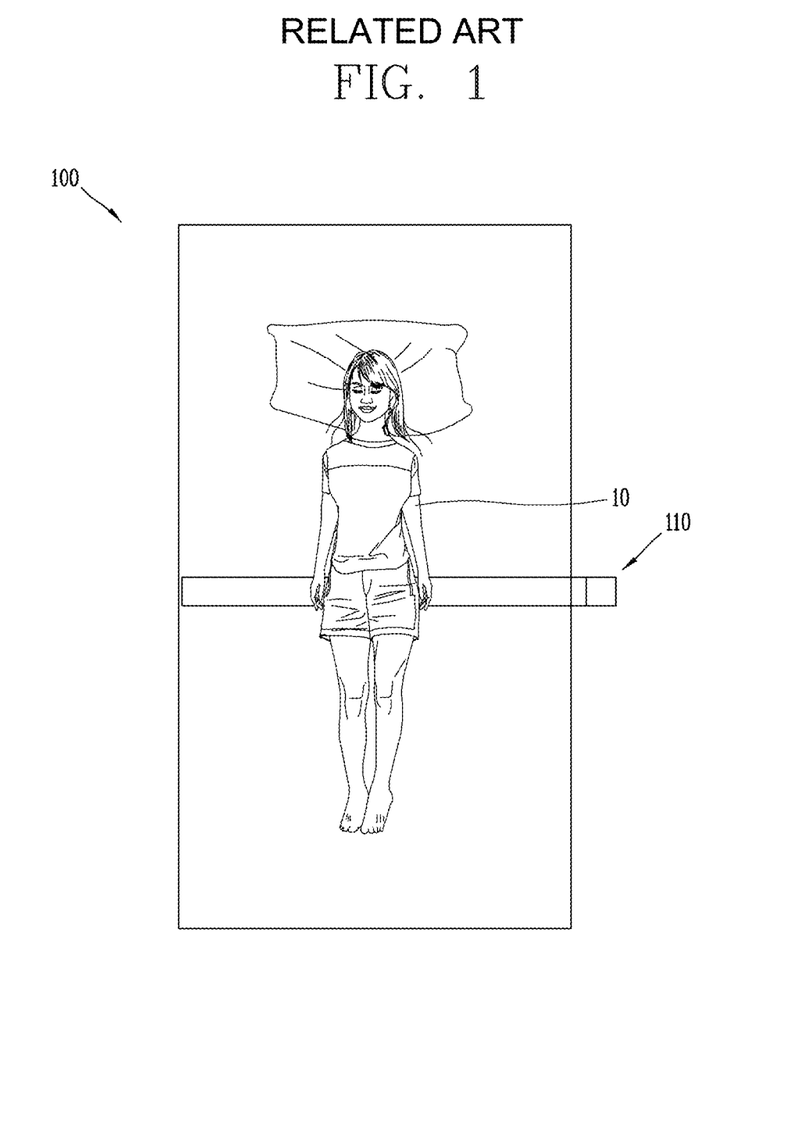
FIGS. 1 and 2 illustrate a human body detection mat in the related art of the present disclosure.
Figure 2:
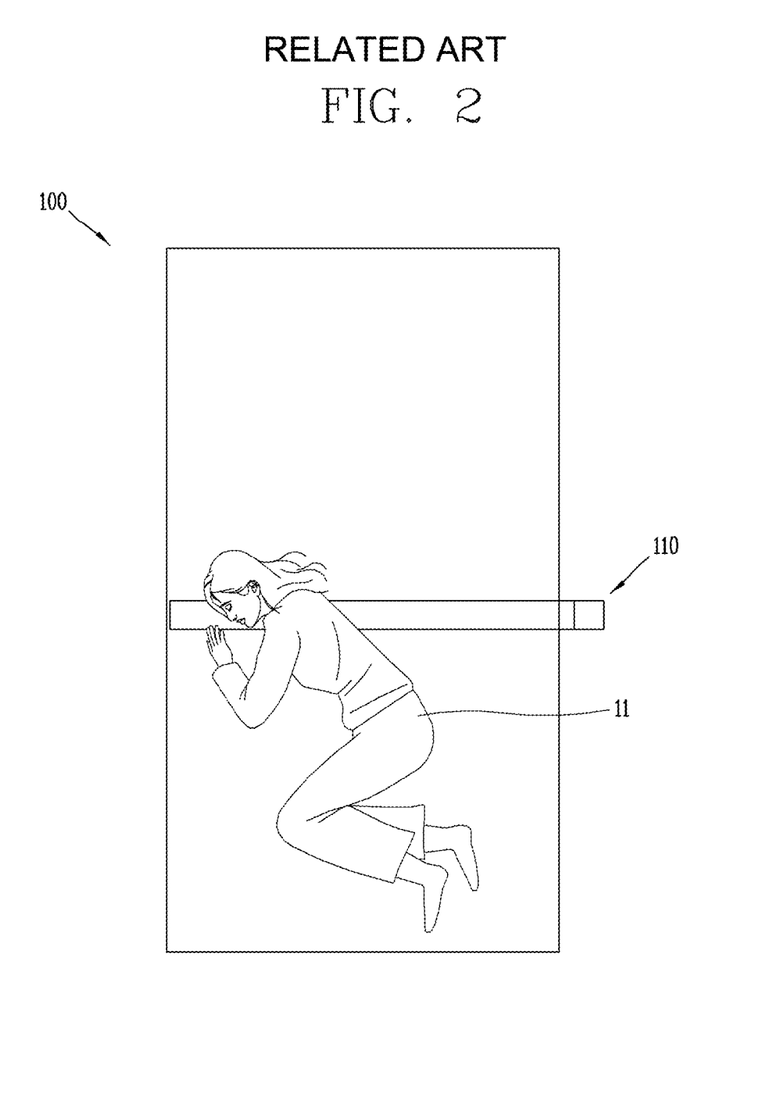

In some examples, as shown in FIG. 1, the user's sleep may be analyzed by placing a sensor 110 at the bottom of bedding. However, the operation of the sensor 110 may depend highly on the user's sleeping posture, and thus the user's sleep analysis may be difficult when the user sleeps in a specific posture. For example, when the user sleeps in a first posture 10 as shown in FIG. 1, the sensor 110 may accurately analyze sleep. However, when the user sleeps in a second posture 21 as shown in FIG. 2, the sensor 110 may not operate for accurate sleep analysis.

In addition, some heating mats are configured such that a user sets a heating temperature and the entire mat is heated at the set temperature. Such heating mats provide low energy efficiency since heat is generated even in a region that is not used by the user.

SUMMARY

An aspect of the present disclosure provides a human body detection mat capable of improving the accuracy of sleep analysis in a non-contact manner.

Furthermore, an aspect of the present disclosure provides a human body detection mat that can be selectively heated in a partial region according to the user's sleep posture.

In addition, an aspect of the present disclosure provides a human body detection mat capable of analyzing sleep regardless of the user's posture.

In order to achieve the foregoing objectives and other objectives, particular implementations of the present disclosure provide a mat that senses an object on the mat. The mat may include a substrate, a plurality of first detection electrode lines disposed on the substrate, and a plurality of second detection electrode lines disposed on the substrate. At least one of the plurality of first detection lines may intersect with at least one of the plurality of second detection electrode lines within a preset region of the substrate. The at least one of the plurality of first detection lines and the at least one of the plurality of second detection lines may have portions that are curved within the preset region of the substrate.

In some implementations, the mat may optionally include one or more of the following features. A part of the at least one of the plurality of first detection electrode lines may be disposed along an edge of the preset region of the substrate. A part of the at least one of the plurality of second detection electrode lines may be disposed along the edge of the preset region of the substrate. The at least one of the plurality of first detection electrode lines may intersect with the at least one of the plurality of second detection electrode lines in a central portion of the preset region of the substrate. At least one of the plurality of first detection electrode lines or the plurality of second detection electrode lines may include a heating electrode configured to generate heat. The at least one of the plurality of first detection electrode lines or the plurality of second detection electrode lines may include a detection electrode that is wound around the heating electrode. The at least one of the plurality of first detection electrode lines or the plurality of second detection electrode lines may include a shielding electrode that is disposed between the heating electrode and the detection electrode and wound around the heating electrode. The at least one of the plurality of first detection electrode lines may intersect with the at least one of the plurality of second detection electrode lines in a plurality of preset regions of the substrate. The mat may include a controller configured to (i) receive a signal from the plurality of first detection electrode lines and the plurality of second detection electrode lines to detect at least one of the plurality of preset regions that is adjacent to the object, and (ii) apply a voltage to the heating electrode that passes through the at least one of the plurality of preset regions such that heat is generated at the at least one of the plurality of regions. The controller may determine the voltage based on the number of the at least one of the plurality of preset regions that is adjacent to the object. The portions of the at least one of the plurality of first detection lines and the at least one of the plurality of second detection lines may be smoothly curved within the preset region of the substrate. The object may include a human body. The plurality of first detection electrode lines may be disposed along a first direction, and the plurality of second detection electrode lines may be disposed along a second direction that intersects with the first direction.

In some implementations, the mat may include a controller configured to detect at least one of the plurality of preset regions that is adjacent to the object at the mat based on signals from the plurality of first detection electrode lines and the plurality of second detection electrode lines. The controller may be configured to generate heat at the heating electrode that passes through the at least one of the plurality of preset regions.

In some implementations, the at least one of the plurality of first detection electrode lines may intersect with the at least one of the plurality of second detection electrode lines in a plurality of preset regions on the substrate. The mat may include a controller configured to (i) receive a signal from the plurality of first detection electrode lines and the plurality of second detection electrode lines to detect at least one of the plurality of preset regions that is adjacent to the object, and (ii) apply a voltage to the heating electrode that passes through the at least one of the plurality of preset regions such that heat is generated at the at least one of the plurality of preset regions. The controller may determine the voltage based on the number of the at least one of the plurality of preset regions that is adjacent to the object.

In some implementations, the mat may include a controller configured to (i) detect at least one of the plurality of preset regions that is adjacent to the object at the mat based on signals from the plurality of first detection electrode lines and the plurality of second detection electrode lines, and (ii) generate heat at the heating electrode that passes through the at least one of the plurality of preset regions.

In order to achieve the foregoing objectives and other objectives, implementations of the present disclosure provides a human body detection mat that senses the movement of a human body. The human body detection mat may include a substrate, a plurality of first detection electrode lines arranged on the substrate and formed along a first direction, and a plurality of second detection electrode lines arranged on the substrate and formed along a second direction intersecting the first direction. The first and second detection electrode lines may intersect with each other within a specific region on the substrate, and may be curved within the specific region.

Part of the first detection electrode line and part of the second detection electrode line may be arranged to be formed along an edge of the specific region.

The first and second detection electrode lines may intersect each other in a central portion of the specific region.

At least one of the first and second detection electrode lines may include a heating electrode that generates heat when a voltage is supplied thereto, and a detection electrode formed to wind the heating electrode.

At least one of the first and second detection electrode lines may further include a shielding electrode disposed between the heating electrode and the detection electrode, and formed to wind the heating electrode.

The first and second detection electrode lines may intersect each other in a plurality of regions on the substrate.

The present disclosure may further include a controller configured to apply a voltage to the heating electrode, and receive a signal generated from the first and second detection electrode lines to detect at least one region adjacent to an external object among the plurality of regions, wherein the controller applies a voltage to allow the heating electrode passing through the at least one region adjacent to the external object among the plurality of regions to generate heat.

The controller may determine the intensity of a voltage applied to the heating electrode based on the number of at least one region adjacent to an external object among the plurality of regions.

A capacitance between detection electrode lines may be improved, thereby improving the sensitivity of a sensor.

Furthermore, according to implementations of the present disclosure, a heating electrode and a detection electrode may be integrally formed, thereby simplifying the structure of the electrode formed on a mat.

In addition, according to implementations of the present disclosure, a plurality of sensing areas may be provided on the mat, thereby allowing a user to analyze the user's sleep even when he or she is located in any region of the mat.

DETAILED DESCRIPTION

Hereinafter, implementations of the present disclosure will be described in detail with reference to the accompanying drawings, and the same or similar elements are designated with the same numeral references in the drawings. Description of known elements or processes may be omitted. It should be understood that the accompanying drawings are merely illustrative, and therefore, they should not be construed to limit the present disclosure. The present disclosure should be construed as being extended to all modifications, equivalents, and substitutes included in the concept and technological scope of the present disclosure.

Hereinafter, a human body detection mat according to implementations of the present disclosure will be described with reference to the accompanying drawings.

Figure 3:
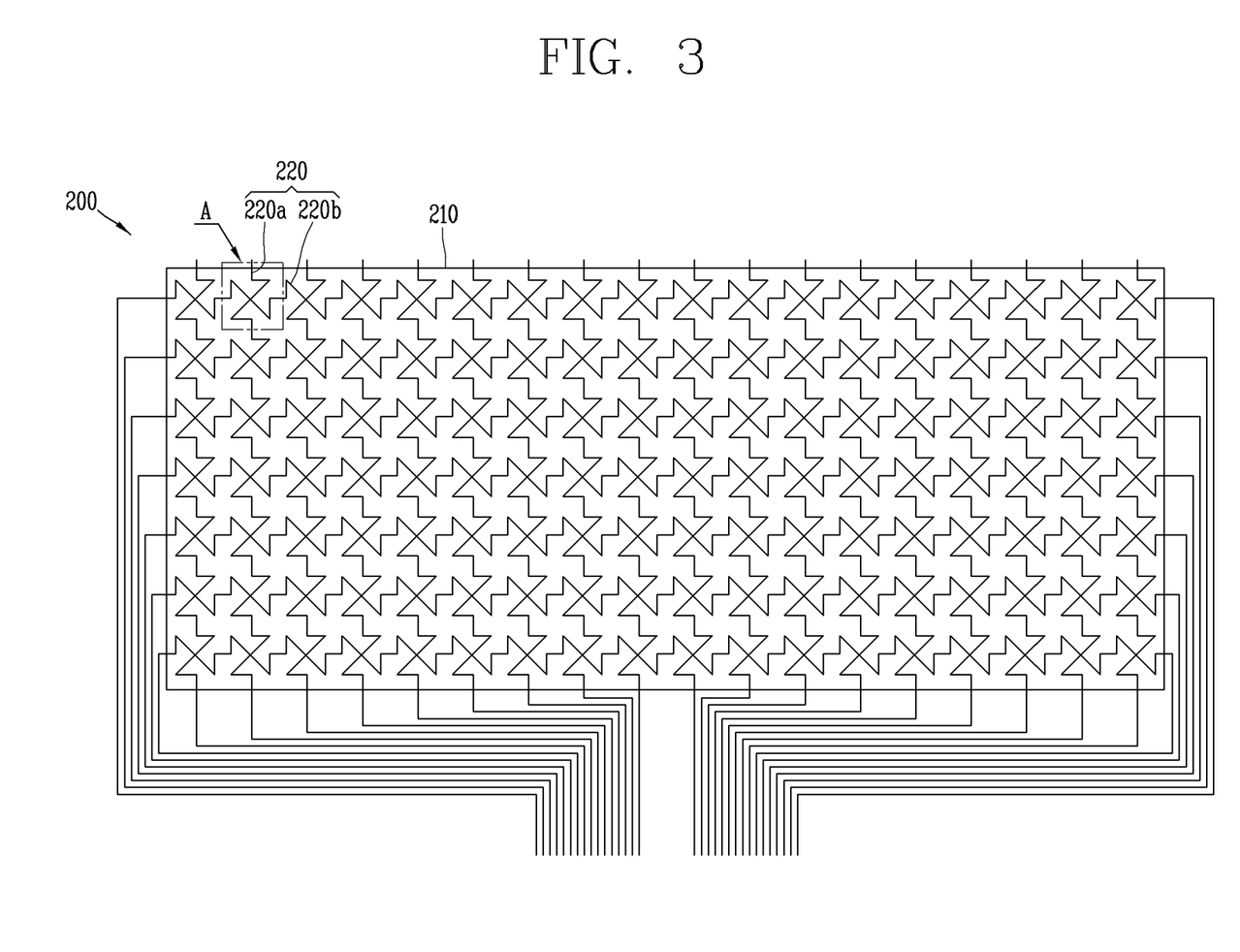
FIG. 3 is a schematic view of an example human body detection mat according to implementations of the present disclosure.

Referring to FIG. 3, the human body detection mat 200 according to implementations of the present disclosure may include a substrate 210, first and second detection electrode lines 220a and 220b, and a controller. The human body detection mat may include more or less components than those described herein.

The substrate 210 is configured to fix the first and second detection electrode lines 220a and 220b thereto. In some implementations, the substrate 210 may be preferably made of a bendable, flexible material so that the mat can be used in various status, such as a fully unfolded state or a partially folded state.

The material of the substrate 210 may include, but not limited to, a bendable and washable material due to the characteristics of the mat.

The first and second detection electrode lines 220a and 220b can be disposed on the substrate 210. The first detection electrode line 220a is disposed along a first direction. In some implementations, a plurality of first detection electrode lines 220a may be provided and arranged side by side, as illustrated in FIG. 3.

On the other hand, the second detection electrode line 220b can be disposed along a second direction intersecting the first direction. In some implementations, a plurality of second detection electrode lines 220b may be provided and arranged side by side, as illustrated in FIG. 3.

Accordingly, each of the first and second detection electrode lines 220a and 220b may intersect with each other at a plurality of points. For example, the first detection electrode line 220a can cross over the second detection electrode line 220b such that the first and second electrode lines 220a and 220b are not electrically connected to each other at the intersection. In some implementations, a region may be defined around a point at which the first and second detection electrode lines 220a and 220b intersect with each other. Such a region can be referred to as an "intersection region". For example, the intersection region may be arbitrarily set. The intersection regions may be defined with the same shape and area, and do not overlap with each other.

Meanwhile, the intersection region may be set to a range that is capable of detecting the approach of an object to the mat using a signal generated at specific intersection points between the first and second detection electrode lines 220a and 220b. For example, the intersection region may be set as a region "A" in FIG. 3.

In some implementations, an intersection point between the first and second detection electrode lines 220a and 220b may operate as a capacitor. For example, the mat 200 can be detect approach of a body to the mat 200 using mutual capacitance between the first and second detection electrode lines 220a and 220b at the intersection point. For example, the mat 200 can be used as a mutual capacitance touch sensor so that, when a human body approaches to the mat 200, a capacitance value of the sensor decreases. At this time, when the reduced capacitance is measured, it may be possible to sense that the body is approaching to the mat. The first and second detection electrode lines act as a capacitor to sense whether a human body is approaching using a change in a capacitance value between the two electrode lines.

When the capacitance value between the two electrode lines is increased, sensing sensitivity may be improved. As described below, the electrode lines have structures that can increase sensing sensitivity in the intersection region.

Figure 4:
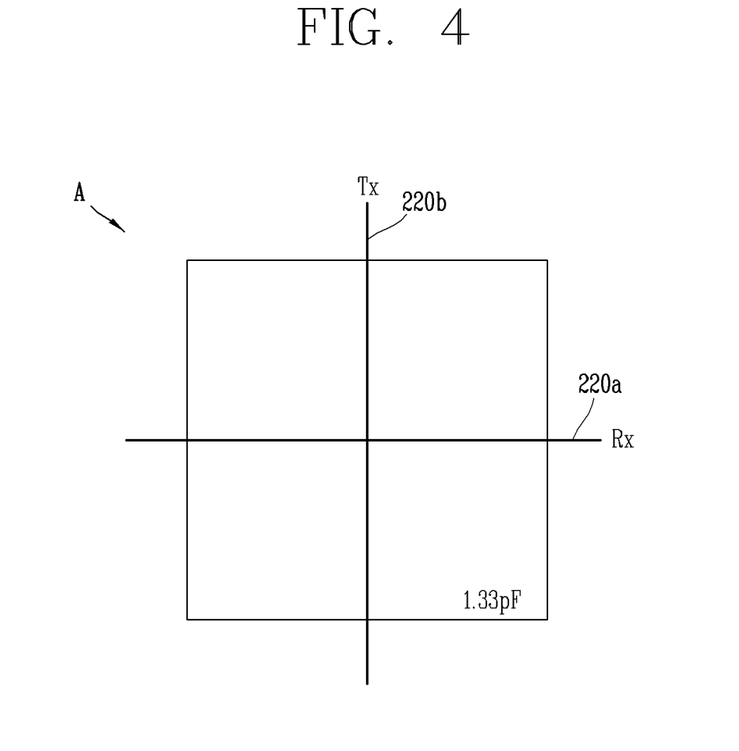
FIG. 4 illustrates a detection electrode of a human body detection mat in the related art of the present disclosure.

Referring to FIG. 4, where a mat is used as a mutual capacitance touch sensor, an intersection region A can be configured such that the first and second detection electrode lines 220a and 220b pass through the intersection region in straight lines. In this case, an electrostatic capacity between the two electrodes may be relatively small.

Figure 5:
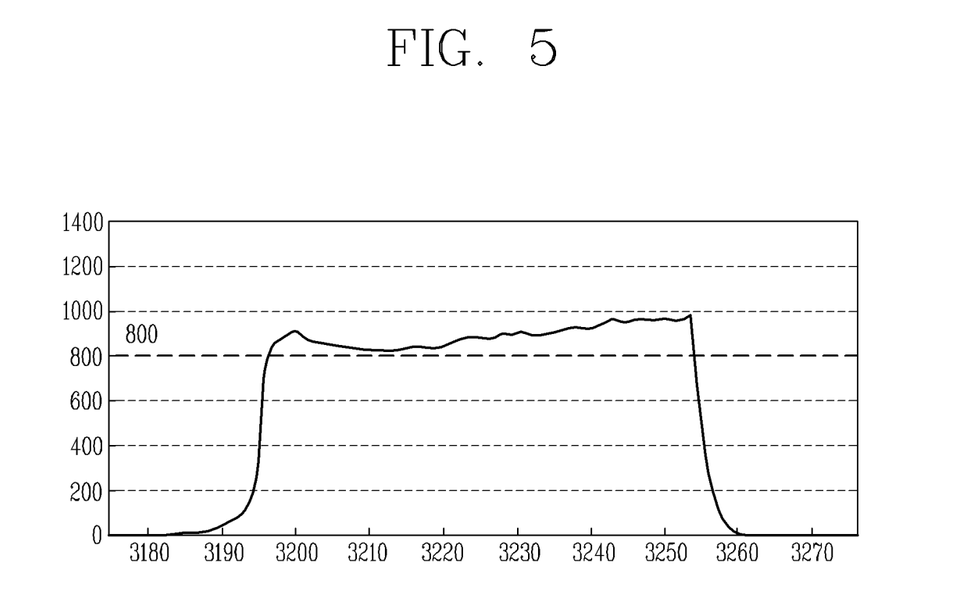
FIG. 5 is a graph showing a sensitivity of the human body detection mat in the related art of the present disclosure.

In implementations where the detection electrode lines are arranged as shown in FIG. 4, a capacitance between the two electrode lines may be 0.85 pF. As shown in FIG. 5, a difference between electrostatic capacitances with and without a physical contact in the intersection region of FIG. 4 may be about 800.

As described below, the present disclosure provides example structures to improve a capacitance between the first and second detection electrode lines, compared to the structure described in FIG. 4.

In some implementations, the first and second detection electrode lines are formed to intersect with each other in the intersection region, and include portions that are bent or flexed (e.g., curved) in the intersection region. For example, referring to portions "a" and "b" in FIG. 6, the first detection electrode line 220a may be bent twice between a boundary of the intersection region and a point where the first detection electrode line 220a intersects with the second detection electrode line 220b. In addition or alternatively, the second detection electrode line 220b can be similarly bent within the intersection region. The detection electrode lines can be bent or flexed in various shapes and/or numbers. For example, the first detection electrode line 220a can be curved at the portions "a" and "b." In other words, the detection electrode lines disposed in the intersection region may be formed in a smoothly curved shape.

Figure 6:
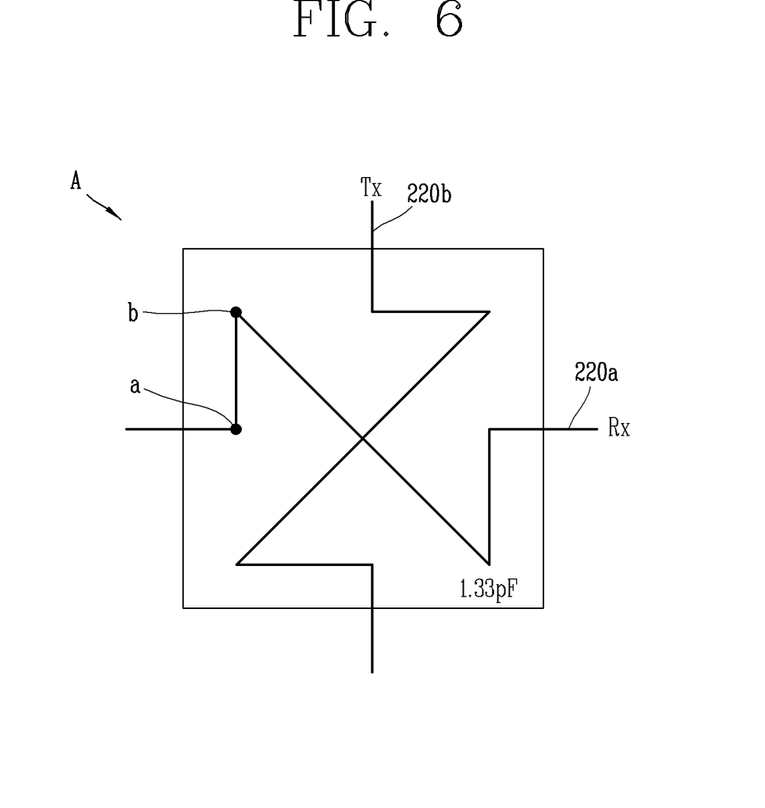
FIG. 6 is an enlarged view of a portion "A" in FIG. 3.

Meanwhile, part of the first detection electrode line 220a and part of the second detection electrode line 220b may be arranged to be formed along an edge of the intersection region. With this configuration, an area enclosed by the first and second detection electrode lines 220a and 220b may be increased around an intersection point between the first detection electrode line 220a and the second detection electrode line 220b.

Figure 7:
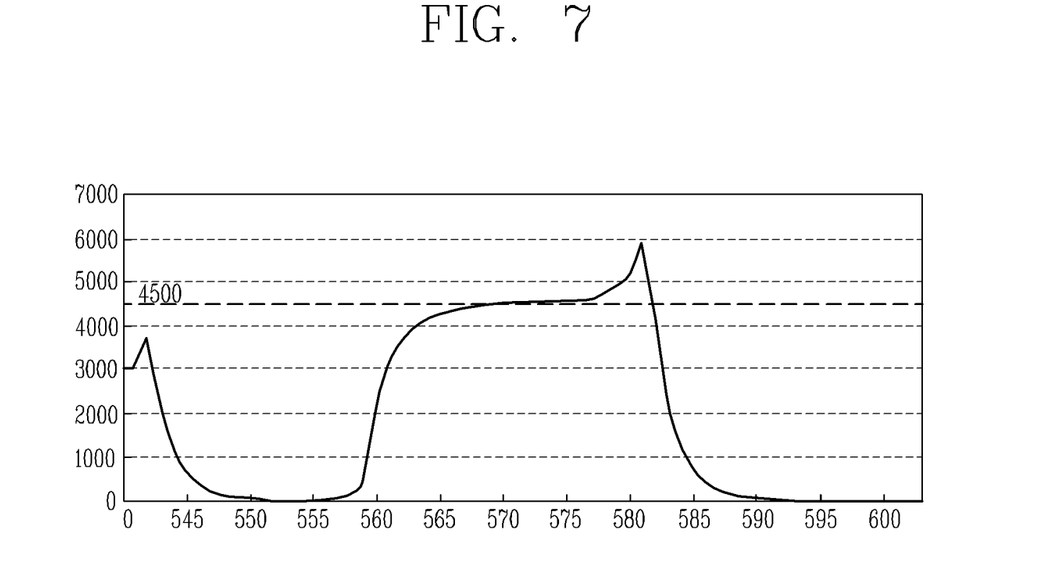
FIG. 7 is a graph showing a sensitivity of the human body detection mat according to implementations of the present disclosure.

In implementations where the detection electrode lines used in a mat are arranged as shown in FIG. 6, a capacitance between the two electrode lines may be 1.33 pF. As shown in FIG. 7, a difference between electrostatic capacitances with and without a physical contact in the intersection region of FIG. 6 may be about 4500.

Comparing between the measurements of FIGS. 5 and 7, it may be seen that the sensitivity of the sensor is increased by 5 times or more. As described above, the structure of the electrode lines according to the present disclosure can improve the sensitivity of the sensor.

In some implementations, a capacitance change between the first and second detection electrode lines 220a and 220b may be based on a distance change between the user and the detection electrode lines even when the electrode lines are not in contact with the user's body. Therefore, using the detection electrode lines, the user's sleep may be analyzed even when the user and the sensor are not in contact with each other.

Since different signals may be generated at each intersection point between the detection electrode lines, information related to the user's sleep may be sensed regardless of where the user is located on the mat.

In some implementations, the human body detection mat according to implementations of the present disclosure may perform a heating function. For this purpose, the mat can include a heating element. For example, the mat can include a heating electrode that generates heat when a voltage is applied to the heating element. In some implementations, the first and second detection electrode lines 220a and 220b and a heating electrode may be arranged on the substrate 210.

As described below, the present disclosure provides a structure in which a detection electrode and a heating electrode are integrated to simplify the structure of the electrodes disposed on a substrate.

Figure 8A:
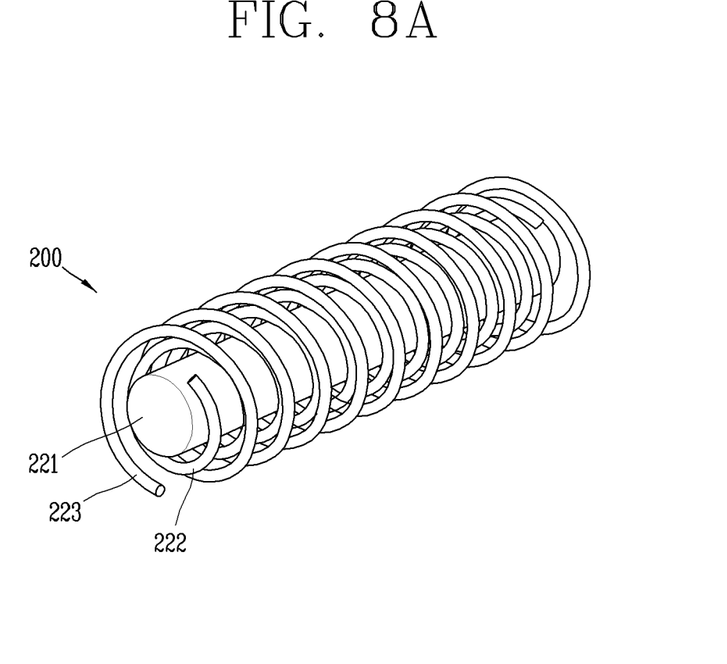
FIGS. 8A, 8B and 8C are perspective, cross-sectional, and plan views of an example detection electrode line according to implementations of the present disclosure.
Figure 8B:
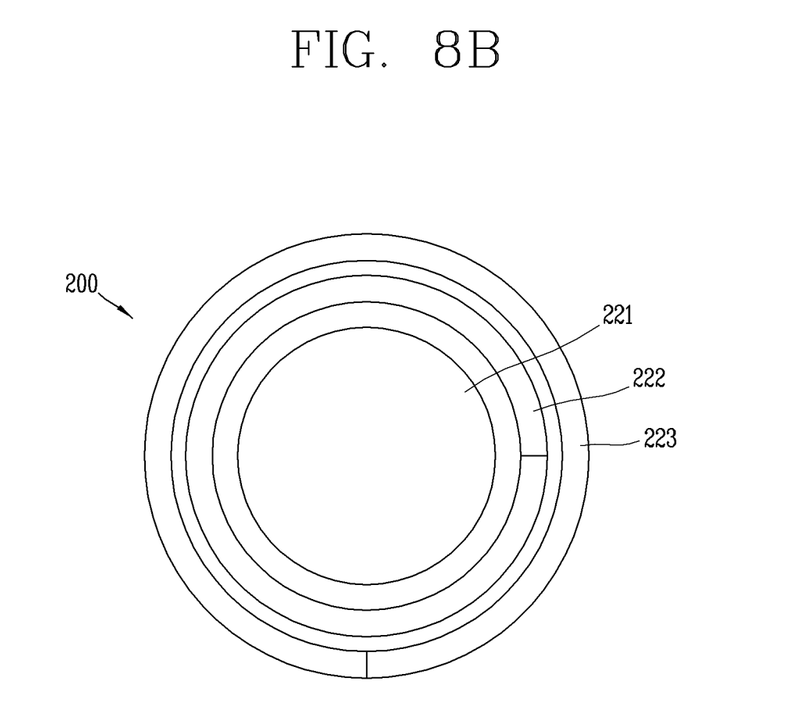
Figure 8C:
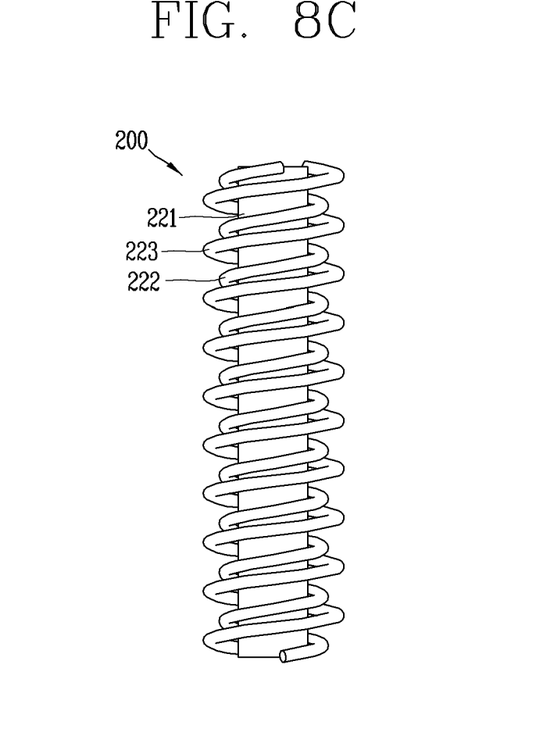

FIGS. 8A, 8B and 8C are perspective, cross-sectional, and plan views, respectively, of an example detection electrode line according to implementations of the present disclosure.

Referring to FIGS. 8A through 8C, at least one of the first and second detection electrode lines 220a and 220b may be provided with a heating electrode 221 formed to generate heat when a voltage is supplied and a detection electrode 223 formed to wind the heating electrode 221. In some implementations, the mat may sense a capacitance change between the detection electrode 223 provided in the first detection electrode line 220a and the detection electrode 223 provided in the second detection electrode line 220b to detect an approaching object.

In some implementations, when a voltage is applied to the heating electrode 221, a strong magnetic field may be generated around the heating electrode 221. This may not only adversely affect the user's health, but also affect the sensitivity of the detection electrode.

In order to prevent those effects, the detection electrode line 220a, 220b may further include a shielding electrode 222 that is disposed between the heating electrode 221 and the detection electrode 223 and that is wound around the heating electrode 221.

When a magnetic field is generated around the heating electrode 221, a magnetic field may also be generated around the shielding electrode 222 to shield the magnetic field that is formed from the heating electrode 221. With this configuration, the shielding electrode 222 may shield the magnetic field generated by the heating electrode 221.

According to the foregoing detection electrode line structure, the heating electrode 221 and the detection electrode 223 may be integrally formed, thereby simplifying the structure of the electrodes 220a, 220b of the mat.

In order to generate heat from the heating electrode 221, a voltage can be applied to the heating electrode 221. In addition, in order to cause a capacitance change between the detection electrodes 223 of the first and second detection electrode lines 220a and 220b, a voltage can be applied to the detection electrode 223 of each of the first and second detection electrode lines 220a and 220b. The controller can apply voltages to the heating electrode 221 and the detection electrode 223, respectively, and measure a capacitance change between the adjacent detection electrodes 223.

Figure 9:
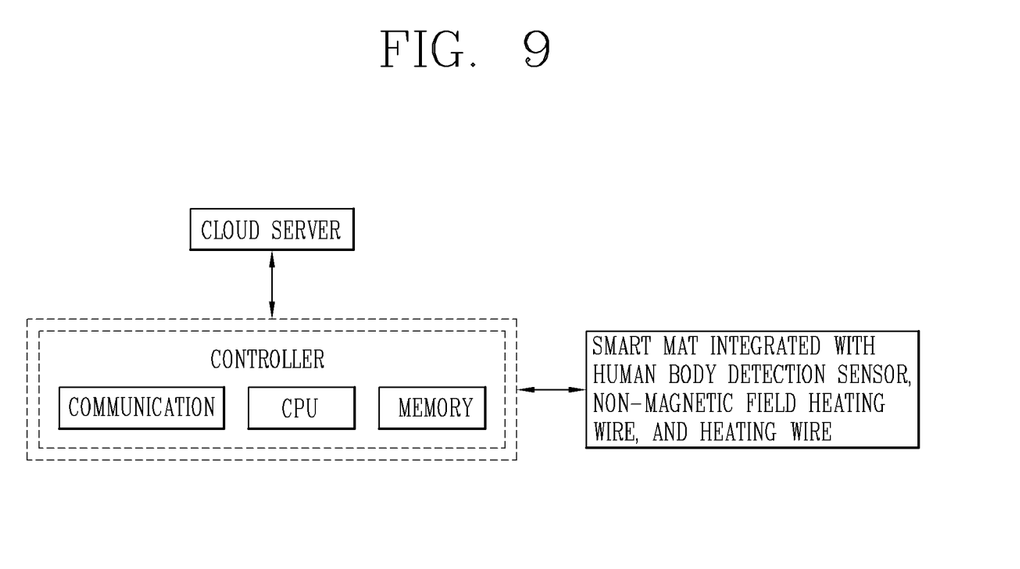
FIG. 9 is a block diagram of an example controller provided in the human body detection mat according to implementations of the present disclosure.
Figure 10:
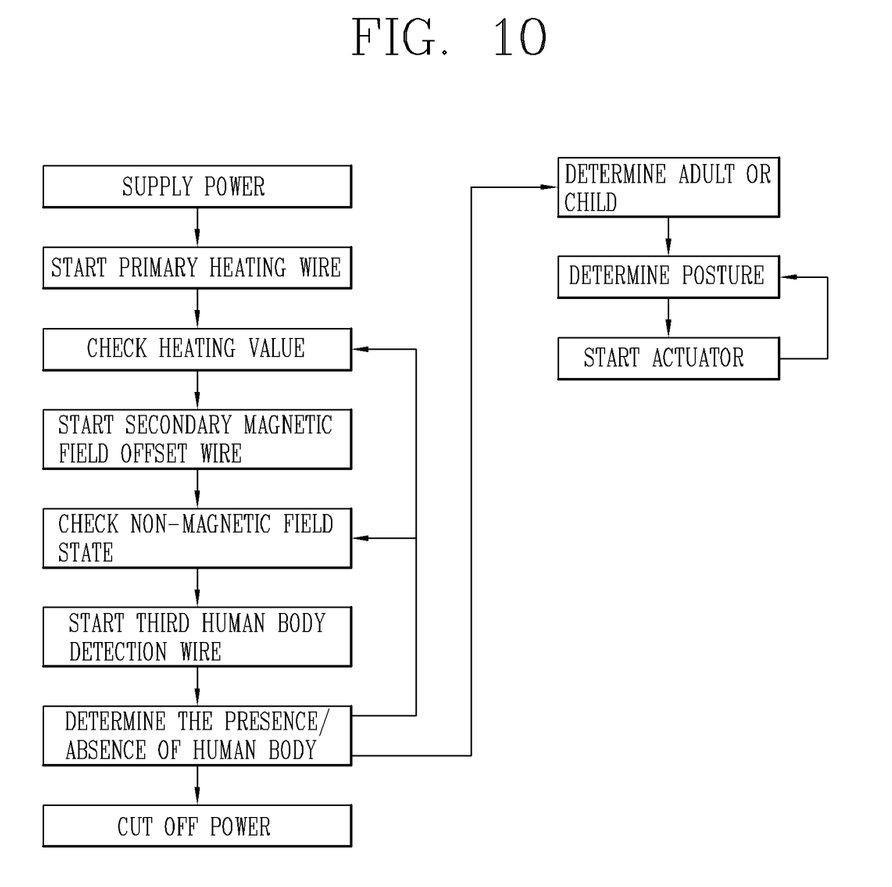
FIG. 10 is a flowchart of an example control method of the human body detection mat.

FIG. 9 is a block diagram of an example controller provided in a human body detection mat according to implementations of the present disclosure, and FIG. 10 is a flowchart illustrating an example control method of the human body detection mat.

In some implementations, as shown in FIG. 9, the controller may include a CPU configured to receive a signal from the detection electrode to analyze a user's sleep, a communication unit configured to transmit and receive data to and from a preset server, a mobile terminal, a cloud server or the like, and a memory configured to store data (e.g., data related to the user). The controller may include a power supply unit configured to supply power to the mat.

The controller may adjust a voltage that is applied to the heating electrode 221 to adjust an amount of heat generated by the mat. In addition, the controller may apply heat to only a part of the plurality of heating electrodes 221 to selectively generate heat from only a partial region of the mat.

The controller may detect a capacitance change between the detection electrodes to analyze a user's sleep, and adjust the heating of the mat using the analyzed result.

In some implementations, referring to FIG. 10, the controller can supply power to the human body detection mat in response to a user request. First, the controller can apply a voltage to the heating electrode. Then, the controller can determine the amount of heat of the heating electrode, and then determine a voltage to the shielding electrode to shield a magnetic field generated around the heating electrode. Then, the controller can apply the determined voltage to the shielding electrode, and then apply a voltage to the detection electrode in a non-magnetic field state.

The controller may determine whether the user is on the mat using a signal generated from the detection electrode, and cut off power applied to the heating electrode and the shielding electrode when it is determined that the user is not on the mat.

On the other hand, when the controller detects a user on the mat using a signal generated from the detection electrode, the number of intersection regions in which the user's body is sensed among a plurality of intersection regions formed on the mat is calculated. The controller can determine a body size of the user based on the calculated number of intersection regions. For example, when the calculated number of intersection regions is less than a preset number, the controller determines that the user is a child.

Based on the determination result, the controller can adjust a voltage that is applied to the heating electrode. In some implementations, when it is determined that the user is a child, the controller may reduce the voltage applied to the heating electrode to prevent burns.

In some implementations, the controller may determine the user's posture and the user's position based on the calculated number of intersection regions and a position where an external object (e.g., the user) is detected. At this time, the controller may selectively apply a voltage only to the heating electrode(s) corresponding to the position where the external object is detected so that heat is generated only in a region occupied by the user. With this configuration, the mat may reduce unnecessary power consumption.

In some implementations, the controller may start an actuator based on the user's posture. An example of the actuator will be described below, for example with reference to FIG. 13.

Figure 11:
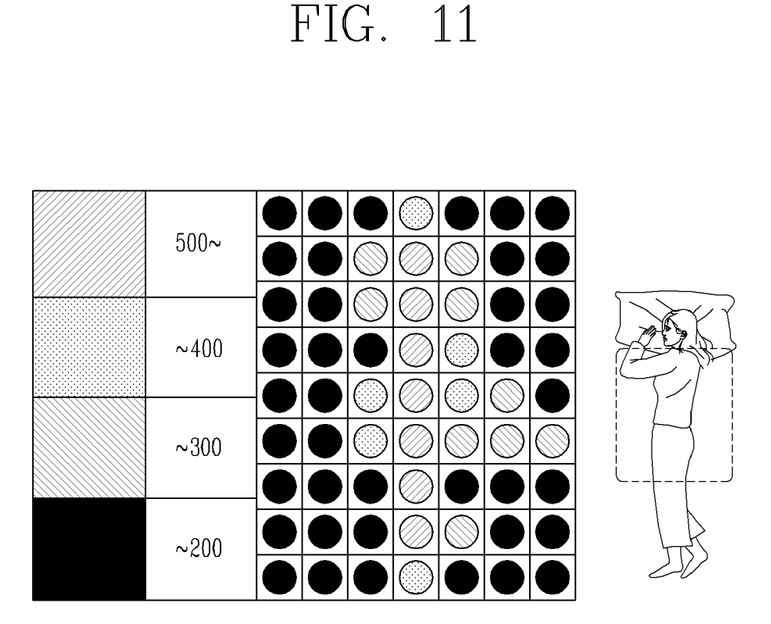
FIGS. 11 and 12 illustrate example use of the human body detection mat according to implementations of the present disclosure.
Figure 12:
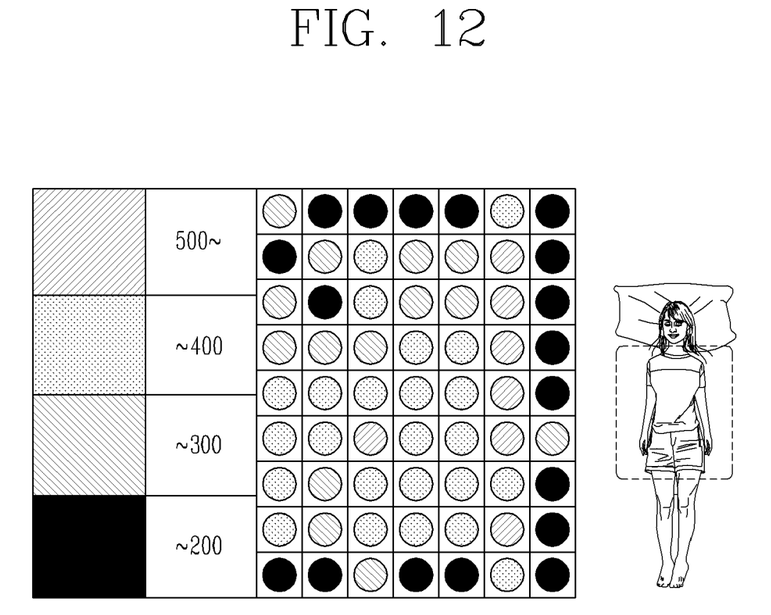

Referring to FIGS. 11 and 12, an example process for performing selective heating based on a user's posture is described in more detail. FIGS. 11 and 12 are conceptual views of an example use of the human body detection mat according to implementations of the present disclosure.

Referring to FIG. 11, when the user sleeps on his or her side, a signal exceeding a threshold (e.g., 200) is generated only in a partial region of a plurality of intersection regions formed on the mat. The controller can determine that the body is in contact with only in a region where the signal intensity exceeds the threshold (e.g., 200) (hereinafter, a body contact region). Then, the controller may calculate the number and position of body contact regions, and determine the user's posture on the basis of this. In the example of FIG. 11, the controller may determine that the user lies on his or her side. At this time, the controller may selectively apply a voltage to the heating electrode(s) to generate heat only in a body contact region.

Referring to FIG. 12, when the user sleeps on his or her back, the number of body contact regions is greater than that of FIG. 11. In this case, the controller may apply a voltage to the entire heating electrode(s) to generate heat from the entire mat.

With this configuration, the mat of the present disclosure may generate heat only in a partial region according to the user's posture.

In some implementations, when it is determined that the user's sleeping posture is incorrect or inappropriate on the mat, the human body detection mat according to implementations of the present disclosure can correct or adjust the user's posture. For example, FIG. 13 is a conceptual view of an example actuator according to implementations of the present disclosure.

Figure 13:
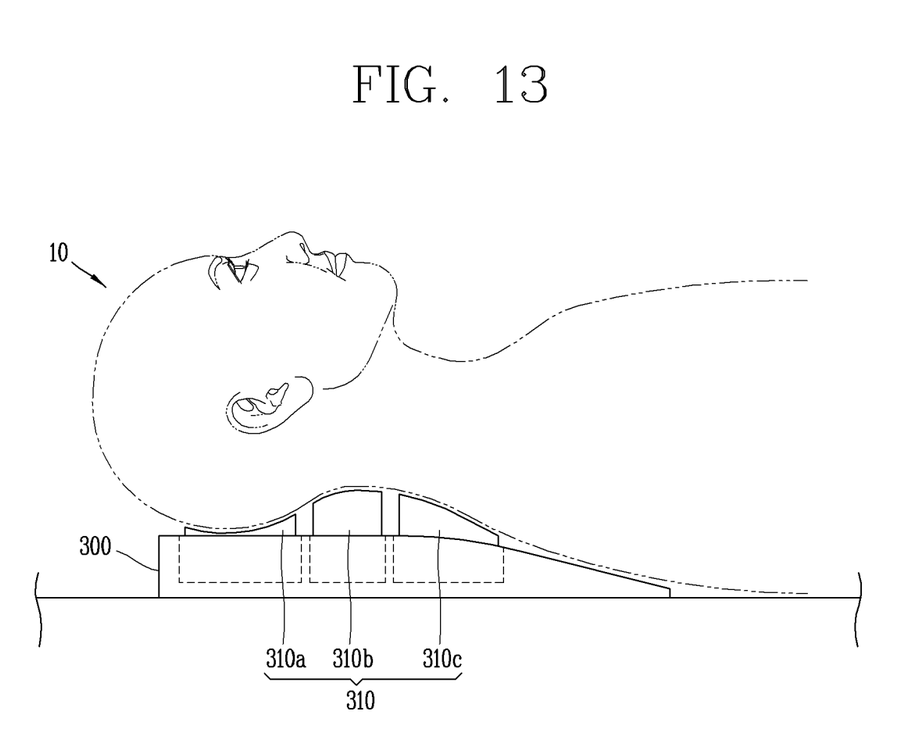
FIG. 13 illustrates an example actuator according to implementations of the present disclosure.

As shown in FIG. 13, the human body detection mat may further include an actuator 300 capable of height adjustment. The actuator 300 may be disposed at a place where the user's neck or waist is located, and configured to form a bend on a mat floor surface. The controller can control the actuator 300 to control the shape of the bend.

For example, the actuator 300 may include a plurality of height adjusters 310. The actuator 300 may adjust the height of each of the height adjusters 310 to form a bend on a bottom surface of the mat.

In some implementations, the controller can determine the user's sleeping posture, and control the actuator 300 to form a bend on the mat floor surface when the sleeping posture is different from a preset posture. With this configuration, the mat of the present disclosure may induce the user to return to his or her correct sleeping posture.

In some implementations, referring to FIG. 13, the mat of the present disclosure may allow the user's airway to be open using the actuator 300 when the user sleeps in a position that is difficult to breath. With this configuration, the mat of the present disclosure may prevent or reduce the user's breathing difficulty during sleep.

In some implementations, the human body detection mat according to implementations of the present disclosure may include at least one of a temperature sensor, a humidity sensor, an illuminance sensor, or an acoustic sensor. The controller may provide information related to sleep based on information sensed by the sensors.

For example, the controller may collectively analyze the ambient temperature, humidity, illuminance, and/or noise level of the mat, and output a sleep environment level (e.g., score) to the user. The more suitable these elements are for the sleeping environment or condition, the higher the level (e.g., score) may be output. The user may check the sleep condition level (e.g., score) and act to increase the sleep condition level. For example, when ambient humidity is low and thus the sleep condition level is low, the user may operate a humidifier or the like to increase the ambient humidity, thereby increasing the sleep condition level.

It is understood to those skilled in the art that the present disclosure can be embodied in other specific forms without departing from the concept and essential characteristics thereof. Furthermore, the detailed description of the present disclosure should not be construed as restrictive in all aspects but considered as illustrative. The scope of the invention should be determined by reasonable interpretation of the appended claims and all changes that come within the equivalent scope of the invention are included in the scope of the invention.

What is claimed is:

1. A mat configured to sense an object on the mat, the mat comprising:
    a substrate;
    a plurality of first detection electrode lines disposed on a plane of the substrate and arranged along a first direction; and
    a plurality of second detection electrode lines disposed on the plane of the substrate and arranged along a second direction intersecting the first direction,
    wherein the plurality of first detection electrode lines and the plurality of second detection electrode lines intersect with one another on the plane of the substrate to thereby define an intersection region on the plane of the substrate within a preset region of the substrate,
    wherein a part of the plurality of first detection electrode lines and a part of the plurality of second detection electrode lines are disposed along an edge of the intersection region, and
    wherein the plurality of first detection electrode lines and the plurality of second detection electrode lines have portions that are curved within the preset region of the substrate.

2. The mat of claim 1, wherein at least one of the plurality of first detection electrode lines or the plurality of second detection electrode lines comprises:
    a heating electrode configured to generate heat;
    a detection electrode that is wound around the heating electrode and defines a first diameter across the heating electrode; and
    a shielding electrode that is disposed between the heating electrode and the detection electrode and wound around the heating electrode, the shielding electrode defining a second diameter less than the first diameter across the heating electrode.

3. The mat of claim 2, wherein the plurality of first detection electrode lines and the plurality of second detection electrode lines intersect one another in a plurality of preset regions of the substrate including the preset region.

4. The mat of claim 3, further comprising:
    a controller configured to:
        receive a signal from the plurality of first detection electrode lines and the plurality of second detection electrode lines to detect at least one of the plurality of preset regions that is adjacent to the object, and
        apply a voltage to the heating electrode that passes through the at least one of the plurality of preset regions such that heat is generated at the at least one of the plurality of preset regions.

5. The mat of claim 4, wherein the controller determines the voltage based on a number of the at least one of the plurality of preset regions that is adjacent to the object.

6. The mat of claim 3, further comprising:
    a controller configured to detect at least one of the plurality of preset regions that is adjacent to the object at the mat based on signals from the plurality of first detection electrode lines and the plurality of second detection electrode lines.

7. The mat of claim 6, wherein the controller is configured to generate heat at the heating electrode that passes through the at least one of the plurality of preset regions.

8. The mat of claim 1, wherein the portions are smoothly curved within the preset region of the substrate.

9. The mat of claim 1, wherein at least one of the plurality of first detection electrode lines intersects with at least one of the plurality of second detection electrode lines in a plurality of preset regions on the substrate.

10. The mat of claim 2, wherein the at least one of the plurality of first detection electrode lines intersects with the at least one of the plurality of second detection electrode lines in a plurality of preset regions on the substrate.

11. The mat of claim 10, further comprising:
    a controller configured to:
        receive a signal from the plurality of first detection electrode lines and the plurality of second detection electrode lines to detect at least one of the plurality of preset regions that is adjacent to the object, and
        apply a voltage to the heating electrode that passes through the at least one of the plurality of preset regions such that heat is generated at the at least one of the plurality of preset regions.

12. The mat of claim 11, wherein the controller determines the voltage based on a number of the at least one of the plurality of preset regions that is adjacent to the object.

13. The mat of claim 10, further comprising:
    a controller configured to (i) detect at least one of the plurality of preset regions that is adjacent to the object at the mat based on signals from the plurality of first detection electrode lines and the plurality of second detection electrode lines, and (ii) generate heat at the heating electrode that passes through the at least one of the plurality of preset regions.

14. The mat of claim 1, wherein the mat is configured to sense a human body on the mat.

* * * * *